United States Patent [19]
Desai et al.

[11] Patent Number: 5,977,369
[45] Date of Patent: *Nov. 2, 1999

[54] PROCESS TO PREPARE DIHYDROPYRIDINE AND DERIVATIVES THEREOF

[75] Inventors: Ranjit Desai, Kendall Park, N.J.; Daniel Alfonso Aguilar, Corpus Christi, Tex.; Mohammad Aslam, Corpus Christi, Tex.; Nicholas Gallegos, Corpus Christi, Tex.

[73] Assignee: Napp Technologies, Inc., Saddle Brook, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/579,758

[22] Filed: Dec. 28, 1995

[51] Int. Cl.⁶ ................................................ C07D 211/86
[52] U.S. Cl. ............................................... 546/321
[58] Field of Search ............................................. 546/321

[56] References Cited

U.S. PATENT DOCUMENTS

| 4,600,778 | 7/1986 | Teller et al. | 546/249 |
| 5,310,917 | 5/1994 | Auerbach | 546/249 |
| 5,403,849 | 4/1995 | Schohe-Loop et al. | 514/340 |

FOREIGN PATENT DOCUMENTS

| 2019711 | 1/1991 | Spain . |
| 1591089 | 6/1981 | United Kingdom . |

OTHER PUBLICATIONS

CA 116:59220 Serra et al, 1992.
CA 114:122068 Serra et al, 1991.
CA 89:109132 Sato et al., 1978.

*Primary Examiner*—Jane Fan
*Attorney, Agent, or Firm*—Pennie & Edmonds LLP

[57] ABSTRACT

A novel process is disclosed for the preparation of dihydropyridine compounds and derivatives thereof, and more particularly felodipine. The process to prepare felodipine involves a two step procedure condensing 2,3-dichlorobenzaldehyde with methyl acetoacetate in the presence of a catalyst system. The resultant benzylidine intermediate is sequentially reacted with ethyl aminocrotonate to provide felodipine. The novelty of the present invention resides in part on (1) a new catalyst system not previously disclosed for the preparation of felodipine, (2) the absence of acid(s), (3) the control of reaction conditions to yield lower amounts of unreacted aldehyde compared to known reactions, (4) a simplified purification process, and (5) formation of negligible quantities of symmetrical diester byproducts.

19 Claims, No Drawings

PROCESS TO PREPARE DIHYDROPYRIDINE AND DERIVATIVES THEREOF

FIELD OF THE INVENTION

The invention relates generally to the preparation of dihydropyridines and derivatives thereof, and more particularly to the preparation of felodipine.

BACKGROUND OF THE INVENTION

Felodipine, Formula 1, is a 1,4 dihydropyridine derivative for use as an antihypertensive and muscle relaxant drug. Other phenyl-1,4 dihydropyridine compounds have been disclosed which have therapeutic activity in the treatment of heart disease, see U.S. Pat. No. 5,310,917.

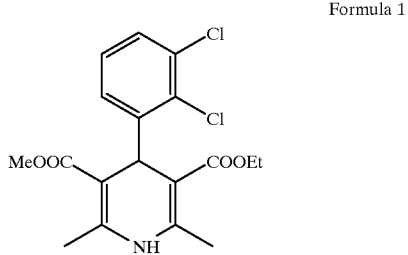

Formula 1

The preparation of felodipine and related compounds typically involves a multistep synthesis, the last step of which usually involves formation of the dihydropyridine ring. U.S. Pat. No. 5,310,917 describes a synthesis involving heating a mixture of a benzylidine with an amino crotonate ester in the presence of a strong acid to yield the desired dihydropyridine product U.S. Pat. No. 4,600,778 describes a process for the preparation of dihydropyridine compounds by reacting a ketocarboxylic ester with an aldehyde, and a catalytic amount of piperidine acetate in an aliphatic alcohol as solvent. Both patents are herein incorporated by reference in their entirety.

Disadvantages with most of the disclosed syntheses for the preparation of dihydropyridine derivatives, and in particular felodipine, include (1) an extractive workup to isolate the desired product; (2) the formation of symmetrical ester byproducts which are difficult to isolate from the desired final compound; (3) use of acids in the reaction which require a neutralization step(s) to remove. The extractive workup and removal of byproducts are labor intensive procedures. From a commercial viewpoint, the use of acids is often costly and environmentally unfriendly. It is preferred to avoid their use and any potential dangers associated with the use of acids.

There is thus a continuing need for a commercially viable, synthetic route for the production of dihydropyridine compounds and, in particular felodipine.

SUMMARY OF THE INVENTION

The following are intended as definitions for terms used herein: aryl refers to aromatic moieties, for example phenyl. Substituents refers to one or more substituent selected from nitro, halo, $C_{1-6}$ alkyl, $C_{1-6}$ alkoxy, hydroxy, trifluoromethyl, and cyano; alkyl and alkoxy chains may be linear or branched; halo or halogen refers to chloro, fluoro, bromo, and iodo. Aryl substitutents may be placed anywhere in the ring.

The present invention relates broadly to the preparation of dihydropyridine compounds and derivatives thereof, and more particularly felodipine. For exemplary purposes, the invention is described in particular detail with respect to the preparation of felodipine. For preparation of other dihydropyridine compounds such as nitedipine, amlodipine, isradipine, and the like, it is understood by those of skill in the art that a similar procedure may be employed. For preparation of compounds other than felodipine, the respective starting aldehyde and ketone compounds are employed.

The process to prepare felodipine involves a two step procedure. First, condensing 2,3-dichlorobenzaldehyde with alkyl, (eg. methyl or ethyl), acetoacetate in the presence of a catalyst system. Second, contacting the resultant benzylidine intermediate with alkyl (eg. methyl or ethyl), aminocrotonate to provide felodipine in high yields. The benzylidine intermediate is optionally isolated after the first step. The novelty of the present invention resides in part on (1) a new catalyst system not previously disclosed for the preparation of the felodipine intermediate, (2) the absence of an acid(s), (3) the control of reaction conditions to yield lower amounts of unreacted aldehyde compared to literature reaction conditions, (4) a simplified purification process, and (5) formation of negligible quantities of symmetrical diester byproducts. This reduction in unreacted aldehyde content is especially important since it affects the outcome of the symmetrical diester impurity formation in the production of felodipine product.

The new catalyst system for the preparation of dihydropyridine compounds comprises a mixture of (I) a carboxylic acid compound having the formula,

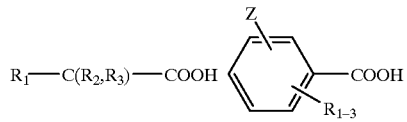

wherein $R_1$, $R_2$, and $R_3$ are independently H, halogen, $C_{1-6}$ alkyl, aryl, substituted aryl, $NO_2$; Z is independently H, halogen, $NO_2$, $OCH_3$, OH and, (II) a secondary amine such as N-methyl benzylamine, dimethylamine, diethylamine, diisopropylamine, diisopropylalkylamine wherein alkyl is $C_{1-6}$, and the like, to form a benzylidine intermediate ("MBI"). The resulting benyzlidine intermediate is then reacted with alkyl or alkylaryl aminocrotonate, e.g., ethylaminocrotonate, methylaminocrotonate, in the absence of an acid to yield the desired product.

Generally, an alcoholic solvent, preferably having between 1 and 6 carbon atoms is employed in the reactions. Optionally, a short chain (e.g. $C_{5-10}$) aliphatic hydrocarbon may be employed as solvent. Suitable reaction conditions for the inventive process include a general temperature range for the first step of the reaction of between about 45° C. to about 65° C. and a reaction time of between about 3 to about 18 hours. A catalytic amount of the catalyst system is employed. Alternatively, the MBI may be treated in-situ with the aminocrotonate derivative to furnish the desired product. Suitable reaction conditions for the second reaction include a temperature range of about reflux of the solvent, for a reaction time of preferably less than about 1 hour.

DETAILED DESCRIPTION OF THE INVENTION

The present invention relates broadly to a process for the preparation of dihydropyridine compounds and particularly to the preparation of felodipine. The synthesis may be applied to the preparation of similar antihypertensive drugs such as amlodipine, cronidipine, diperdipine, furaldipine, isradipine, lacidipine, manidipine, mepirodipine, nifedipine, nivaldipine, nimodipine, nisoldipine, nitendipine, sagandipine and taludipine and the like. The following synthetic scheme illustrates a reaction sequence for the production of felodipine.

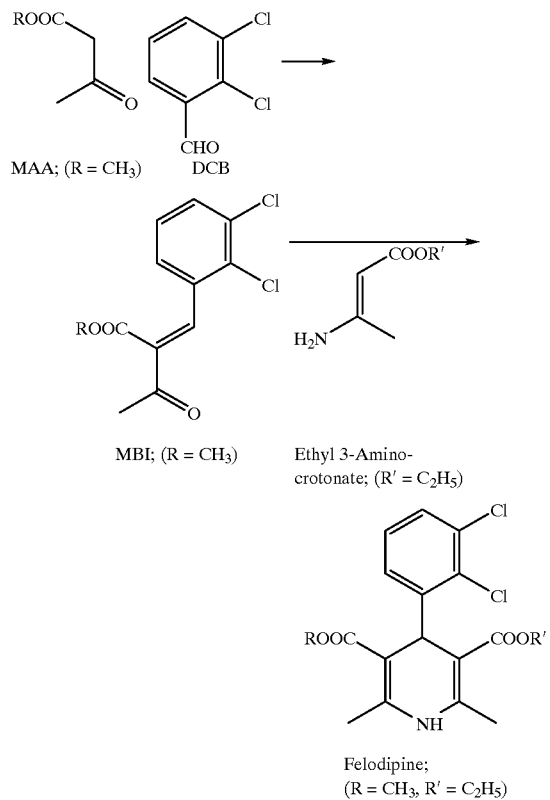

R and R' are $C_{1-6}$ alkyl, preferably $C_{1-2}$. When R is $C_1$, MAA is methyl acetoacetate; DCB is 2,3-dichlorobenzaldehyde; when R is $C_1$, MBI is methyl benzylidine intermediate. EAC is Ethyl 3-aminocrotonate.

It is understood that the above scheme is intended for exemplary and non-limiting purposes. The starting materials for the reactions are well known in the art and generally commercially available or synthesized employing published reaction routes.

The present invention relates broadly to a process for the preparation of a dihydropyridine compound comprising contacting under suitable reaction conditions (a) a compound of formula 2

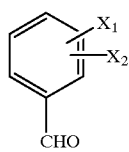

wherein $X_1$ and $X_2$ are same or different substituents selected from the group consisting of H, $C_{1-6}$ alkyl, preferably $C_{1-2}$, $C_{1-6}$ alkoxy, $C_{1-6}$ alkylaryl, halo, aryl, or substituted aryl, with a compound of formula 3

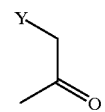

wherein Y is COOR, wherein R is $C_{1-6}$ alkyl, preferably $C_{1-2}$, and a catalytic amount of a mixture of (I) a carboxylic acid compound having the formula

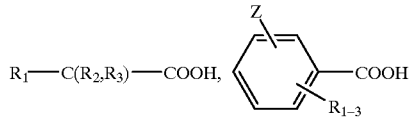

wherein $R_1$, $R_2$, and $R_3$ are independently H, halogen, $C_{1-6}$ alkyl, $C_{1-6}$ alkoxy, alkylaryl, aryl and substituted aryl wherein substitutents may be in any position; Z is independently H, halogen, $NO_2$, $OCH_3$, OH, and, (II) a substituted or unsubstituted secondary amine, such as a dialkyl amine, such as diethylamine dimethylamine, diisopropylamine, N-methyl benzylamine, and the like, to form a benzylidine intermediate; and, (b) contacting said benzylidine intermediate with a suitably substituted enamine in the absence of an acid.

More particularly, the present invention relates to the preparation of felodipine comprising contacting under suitable reaction conditions (a) 2,3-dichlorobenzaldehyde, methyl acetoacetate, and a catalytic amount of an carboxylate salt of an amine which salt may comprise a mixture of (I) and (II) as identified above to form a benzylidine intermediate; and, (b) contacting said benzylidine intermediate with EAC in the absence of an acid.

The reactions will be described below relative to each reaction step for the preparation of felodipine.

STEP (A)

One embodiment of the present invention involves, as step (a), the synthesis of methyl benzylidine as an intermediate (MBI). 2,3-dichlorobenzaldehyde is condensed with methyl acetoacetate in the presence of a catalytic amount of an carboxylate salt of an amine. Generally the reaction is conducted in an alcoholic solvent at a temperature in the range of about 45° C. to about 65° C., at atmospheric pressures, and for a time of about 3 to about 18 hours.

Another embodiment of step(a) employs aromatic aldehyde compounds having the general formula 2

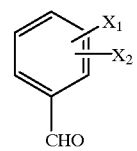

wherein $X_1$ and $X_2$ are as previously defined.

Exemplary aromatic benzaldehydes include but are not limited to, 2- or 3-nitrobenzaldehyde, 2,3-diichlorobenzaldehyde, 2,1,3-benzoxadiazole-4-aldehyde, and the like.

Exemplary ketocarboxylic acids include but are not limited to ethyl acetoacetate, methyl acetoacetate, cyclopropyl acetoacetate, isopropylacetoacetate, and the like.

Generally the aldehyde and carboxylic acid are reacted in a molar ratio of about 0.5–2.0, preferably about 0.8–1.0 and most preferably about 0.9.

Exemplary catalyst systems include but are not limited to carboxylate or benzoate salts of amines such as the salt mixture of N-methyl benzylamine, diethylamine, dimethylamine, isopropylethylamine, isopropylmethylamine, and the like, and chloroacetic acid, phenylacetic acid, benzoic acid, and the like. Catalyst is employed in a sufficient amount to catalyze the reaction. The catalyst is generally added in amounts of about 0.04 to about 0.20 equivalents of aldehyde, preferably about 0.6–0.10, and most preferably about 0.06–0.08 molar ratio. The catalyst component (I) may contain any halogen. Chlorine is a preferred halogen substitutent primarily due to commercial availability and cost. It is important to employ a carboxylic acid as a catalyst component. Other useful catalyst components include, but are limited to, dihalogen compounds, e.g. dichloroacetic acid, phenylacetic acid, benzoic acid, and the like.

MBI exists as two isomers (E and Z) and the reaction of 2,3-dichlorobenzaldehyde and methyl acetoacetate generally reaches an equilibrium after about 4 hours. This mixture of isomers consists of about 45:55 ratio of E to Z isomer and we have found that predominately one of the two isomers precipitates from solution. The more soluble isomer remains in solution in the filtrate. The filtrate is thermally isomerized to regenerate the thermodynamic mixture of isomers that allows us to isolate a second crop and increase our yield.

The condensation of step (a) is preferably carried out in a solvent that facilitates the reaction. It has also been found that satisfactory selectivity and yield can be obtained by carrying out the process of step (a) in alcoholic solvents. Generally, an initial concentration of aldehyde of about 10 to about 20 percent (%) by weight (wt) in the solvent is employed. Suitable reaction solvents for step (a) include alcohols having between about 1 and 6 carbon atoms and short chain (e.g. $C_{5-10}$) aliphatic hydrocarbons. Exemplary alcohols include methanol, ethanol, isopropanol, with a preference for isopropanol. Exemplary aliphatic or cycloaliphatic solvents include hexane and cyclohexane. Additional optional solvents which are less preferred include organic aromatics such as benzene, toluene, and the like, and halogenated solvents such as dichloromethane, dichloroethane, chloroform, and the like.

The time of the reaction is only that necessary to complete the reaction and the reaction can generally be carried out at elevated temperature (e.g., refluxing isopropanol) under atmospheric conditions. Generally the reaction proceeds in about 3 to about 18 hours, preferably s about 3 to about 10 hours, and most preferably about 4–6 hours.

In one embodiment of the present invention, 2,3-dichlorobenzaldehyde is condensed with methyl acetoacetate in isopropanol and heated to an internal temperature of about 60° C. The mixture is concentrated by removing distillate at about 45–60° C. and the contents cooled gradually. The resultant precipitated MBI is removed by filtration, washed with isopropanol and dried in vacuo (preferably at less than 40° C.). The reaction proceeded in about 3–4 hours. If desired, a second crop may be isolated from the recovered filtrate.

Optionally, instead of isolating the MBI, it may remain in the reaction vessel and be utilized as is for the reaction of step (B).

STEP (B)

The benzylidine product of step 1 is condensed with a suitably substituted enamine, such as mentioned previously, in a refluxing alcoholic solvent, preferably isopropanol. In one embodiment of the present invention, the MBI formed during step (A) is preferably isolated and dried and reacted with EAC. Preferably, the MBI is dissolved in isopropanol (preferably in a ratio of approximately 1 ml isopropanol per mmol MBI), and the contents brought to reflux.

The felodipine reaction is sensitive to the amount of EAC charged during step (B). It has been found that when the EAC charge exceeds about 1 equivalent (per MBI), symmetrical diesters are produced, especially the diethyl ester. These ester impurities are difficult to remove in subsequent purification, therefore, it is strongly recommended to avoid their formation by careful monitor of the initial amount of EAC charged to the reaction.

In addition to the EAC charge sensitivity, the felodipine reaction of step (B) is sensitive to reaction time, particularly in isopropanol solvent. The amount of symmetrical diesters increases with time at the expense of the felodipine product. The sensitivity of the felodipine reaction to time appears to be less pronounced than the sensitivity of the reaction to the EAC charge.

To the refluxing MBI/isopropanol solution described above, is added an isopropanol solution of EAC (approximately 0.9 equivalents relative to MBI) at such a rate that the internal temperature of the reaction is maintained at reflux (approx. 83° C. or about 10 minutes addition time). The resulting mixture is refluxed for about 60–70 minutes, preferably about 40 to about 60 minutes, and then the reaction temperature is reduced quickly to below 50° C. This may be accomplished in a variety of methods known to the art. The method employed herein involved removing the heat source, adding isopropanol to the reaction, and vacuum distilling the isopropanol solvent. The vacuum distillation is preferably performed at less than 50° C. to obtain a residue of crude felodipine.

U.S. Pat. No. '917 describes the use of strong acid in this step and indicates the acid accelerates the reaction and improves purity of the product. We have found that the acid is not necessary to obtain the final felodipine product in high purity. It is strongly recommended to maintain the reaction at reflux less than 60 minutes. As mentioned, a greater time generally results in formation of symmetrically substituted symmetrical ester byproducts. It has been found that if the reaction is performed for less than 1 hour, symmetrical ester byproducts are generally maintained to about or less than 1% in the reaction. The reaction is generally monitored by liquid chromatography (or some other like means of monitoring known to those skilled in the art) to follow the formation of desired product and byproducts.

Additionally, if the reaction is performed for less than one hour, the amount of unreacted aldehyde is usually less than 1:1.5%. Sodium bisulfite may be employed to remove any unreacted aldehyde from the reaction of step (A).

Advantages of the present invention include lack of use of hazardous solvents, and a more efficient, cost effective method to produce felodipine.

STEP (C)

Purification

During the felodipine reaction of step (B), about 5–10% regioisomer

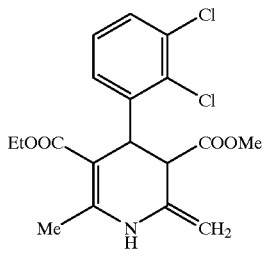

(exocyclic double bond) is formed. This regioisomer co-precipitates with felodipine and therefore must be converted to felodipine prior to isolation of the desired product. We have found that, contrary to the art, this may be accomplished in the absence of an acid by refluxing the crude felodipine in an inert solvent such as cyclohexane. Generally, most solvents having a boiling point of at least about 80° C. are sufficient for this purification step. Not wishing to be bound by theory, it appears that the cyclohexane reflux thermally converts the regioisomer to felodipine. Generally, this conversion will be accomplished in about 6 to about 20 hours.

Cyclohexane (ca. 2–6 parts) is added to the crude residue of step (B) and a distillation is performed at below 50° C. This procedure is repeated twice, preferably three times with the final residue/cyclohexane addition refluxing at about 80–85° C. at atmospheric pressure for about 6 hours. Provided the thermal conversion of the regioisomer has occurred, the distillation/reflux may be performed for shorter or longer periods of time if desired. It is preferred to monitor the conversion by suitable means to determine complete conversion.

Once converted, the resultant felodipine product is in a slurry and may be cooled to about 30–35° C. to obtain felodipine solids which are subsequently isolated and washed with cyclohexane.

The moist felodipine solids are dissolved in hot methyl tert-butyl ether (MTBE). Alternate solvent systems include ethanol/water mixture, aliphatic, cycloaliphatic such as cyclohexane, or aromatic hydrocarbons. Any solvent or solvent system is acceptable for use at this step provided that the felodipine is at least partially soluble in the hot solvent mixture. Generally the mixture may be hot filtered to clarify the solution. The solution is concentrated, by conventional means, and the MTBE distillates collected. Cyclohexane is added to the resultant residue in an amount to prepare an approximate 80:20 (w/w) MTBE:cyclohexane solvent system and heated. The solution is cooled and the recrystallized felodipine is isolated at about 30–35° C. The solids are further washed in an 20:80 (w/w) MTBE:cyclohexane mixed solvent system, followed by a cyclohexane wash and dried in vacuo to afford felodipine solids in a purity of greater than 99.5% (area % in accordance with HPLC).

Relative to the art, the present invention has now eliminated acidic solvents, and provides a simplified purification process.

EXAMPLES

The following examples are intended to illustrate one embodiment of the present invention and are not intended to limit the scope or utility thereof.

Example 1

Step A. Synthesis of MBI

A single necked 1-L flask with charged with about 87.5 g of 2,3-dichlorobenzaldehyde (approx. 0.5 mol, 1.0 equiv), 2.8 g of chloroacetic acid (0.030 mol, 0.06 equiv), 662 mL of isopropanol, 63.8 g methyl acetoacetate (0.55 mol, 1.1 equiv), and 3.6 g of N-methylbenzylamine (0.03 mol, 0.06 equiv). The flask was placed on a rotary evaporator equipped with a thermowell (via steam duct) for monitoring internal temperature and the flask heated and agitated to bring flask contents up to about 60±5° C. for approximately 3 hr. The mixture was concentrated by removing 250–350 g of distillate at about 45–65° C. (internal temperature) and the content gradually cooled in an ice bath to about 0–5° C. The precipitated MBI solids were isolated by filtration and washed with about 70 g of isopropanol and added to the filtrate.

The combined filtrates and wash were re-heated to about 60±5° C. for 1 hr, and concentrated by removing about 175–225 g of distillate at about 45–65° C. (internal temperature). The contents were again gradually cooled in an ice bath to collect a second crop of MBI solids which were isolated by filtration on the same filter funnel containing the first crop solids. The combined first and second crop solids were washed with 2×70 g of isopropanol and dried in vacuo (<40° C.).

Step B. Synthesis of Felodipine from MBI

A 2 L flask was equipped with a mechanical agitator, nitrogen purge, reflux condenser, addition funnel and internal temperature probe and charged with the MBI solids (about 95 g, 0.35 mol, 1.0 equiv) and 266 ml isopropanol and the contents are brought to reflux. A solution of about 0.90 equiv of ethyl 3-aminocrotonate (about 40.4 g EAC for 95 g MBI charge, 0.31 mol, 0.9 equiv) in 96 mL of isopropanol was added to the refluxing solution at such a rate that the internal temperature was maintained at reflux (ca. 83° C. or about 10 min addition time). The resulting mixture was kept at reflux for 60–70 min, then the temperature brought down to below 50° C. by (1) removing heat source, (2) adding 96 niL of isopropanol, and (3) vacuum distillation of isopropanol.

The vacuum distillation was performed at below 50° C. to remove approximately 200– 300 g of overhead. Cyclohexane (155 g) was added to the residue and the distillation continued at below 50° C. to remove an additional 100–150 g of overhead. Another cyclohexane (155 g) portion was added to the residue and the distillation continued at below 50° C. to remove yet another 100–150 g of overhead. A third cyclohexane (780 g) portion was added and the contents brought to atmospheric reflux (ca. 80–85° C.) for about 6 hrs. The slurry was cooled to about 30–35° C. and the crude felodipine isolated by filtration and washed with 50 g cyclohexane.

Step C. Purification

The moist crude felodipine solids were dissolved in about 550 g of methyl tert-butyl ether (MTBE) and hot filtered to clarify the solution. The dissolving flask and filter were rinsed with an additional 30 g of MTBE, which was added to the original hot filtrate. The MTBE solution was placed in a flask equipped with agitator, nitrogen purge, heat source, temperature probe, distillation head and receiver. The mixture was concentrated by atmospheric distillation to remove MTBE (ca. 550° C. internal temperature). Once 100–250 g of distillate have been collected, cyclohexane was added in an amount to prepare approximately an 80:20 (w/w) MTBE-:cyclohexane solvent system. The resultant solution was cooled and the recrystallized Felodipine was isolated at about 30–35° C. The recrystallized felodipine solids were further washed with 1×70 g of 20:80 (w/w) MTBE:cyclohexane and 1×70 g of cyclohexane. The solids were dried in vacuo to afford 45–70 g of pure felodipine solids.

Theoretical Yield: 172.4 g (MW 383) based on ethyl 3-aminocrotonate

Isolated Yield: 45–70 g (26–40% yield)

Isolated Purity: >99.5% area % by HPLC

Example 2

Step A. Synthesis of MBI (In a single reaction vessel, without the isolation of MBI)

In a four necked 3 liter jacketed flask, a solution of 2,3-dichlorobenzaldehyde (about 175 g 1.0 mole) chloroacetic acid (about 18.9 g. 0.2 mole) and N-methylbenzyl amine (about 24.2 g, 0.2 mole) in 2-propanol (about 750 ml) was stirred vigorously for about 30 minutes at room temperature. A solution of methyl acetoacetate (about 116.1 g., 1.0 mole) in isopropanol was added to the dichlorobenzaldehyde solution and stirred at about 40° C. for about 15 hours. Isopropanol was removed under reduced pressure and ethyl acetate (about 500 ml) was added to the residue. The resulting viscous yellow orange oily residue was dissolved in ethyl acetate and washed with aqueous 10% $NaHCO_3$. To remove traces of unreacted dichlorobenzaldehyde, 7.5 molar excess of $NaHSO_3$ solution in isopropanol/water was added to the ethyl acetate solution and stirred for about 2 hours, followed by repeated water washes. The ethyl acetate solution was concentrated under reduced pressure.

Step B. Synthesis of Felodipine

The resulting MBI was dissolved in isopropanol and brought to reflux. Ethyl 3-aminocrotonate (about 100.9 g, 0.78 mole) in isopropanol was added to the MBI at such a rate to maintain the internal temperature at approximately 83° C. the resulting mixture was refluxed for about 1 hour and the temperature then cooled to about 40–50° C. Excess isopropanol was removed maintaining the internal temperature of the reaction at between about 40 and 45° C. Hexane was then added to the residue, removed, and repeated. The temperature was then brought to room temperature. During this time, the oily residue transformed to granular solids. Hexane was decanted off to yield solid felodipine, along with unreacted MBI, symmetrical dimethyl dihydropyridine along, and dichlorobenzaldehyde.

Step C. Purification

The residue was dissolved in MBTE and brought to reflux. The solution was concentrated and cooled linearly over a period of about 3 hours to ambient temperature. The solids which formed were filtered and washed with MBTE/hexane solution to provide felodipine in about 99.4% purity.

Example 3

Step A. Synthesis of MBI (Isolation of MBI)

In a four necked, 3 liter jacketed flask, a solution of 2,3-dichlorobenzaldehyde (about 612 g, 3.5 mole), chloroacetic acid (about 66.1 g, 0.7 mole) and N-methylbenzylamine (about 84.8 g, 0.7 mole) in isopropanol were stirred vigorously for about 30 minutes. A solution of methyl acetoacetate (about 406 g, 3.5 mole) in isopropanol was added in one lot, at room temperature, stirred and the temperature increased to about 40° C. for about 15 hrs. Isopropanol was removed under vacuo and ethyl acetate added to the resulting residue and concentrated. The resulting viscous yellow-orange oily residue was redissolved in ethylacetate and washed with aqueous 10% $NaHCO_3$ solution followed by a $NaHSO_3$ wash and a water wash. The ethyl acetate solution was then concentrated to furnish a stirrable yellow orange oil. After drying this oil under high vacuum (about 1 mm Hg, ambient temperature), a yellow crystalline solid mass of MBI was obtained (MP 54–56° C.).

Step B. Synthesis of Felodipine

In a four necked, 3 liter flask, a solution of MBI (about 268.4 g, 0.98 mole) in isopropanol was brought to reflux and a solution of ethyl 3-aminocrotonate (about 114.2 g, 0.8 mole) in isopropanol was added at such a rate to maintain the internal temperature at about 81–83° C. and refluxed for about 1 hour. The temperature of the reaction was then lowered to about 40–50° C. and excess isopropanol removed under reduced pressure maintaining the internal temperature at about 40–45° C. to furnish a viscous yellow orange residue. LC analysis of this residue indicated about 75% felodipine product, 13% MBI, 4% dichlorobenzaldehyde and about 0.5% symmetrical dimethyl dihydropyridine analog and about 0.4% diethyl dihydropyridine analog. Hexane was added to the residue and the suspension stirred under reflux for about 1 hr. The temperature was allowed to fall to about 40° C. during which solids formed. The solids were filtered and washed with fresh hexane and dried to yield felodipine in about 62% yield. LC analysis indicated about 92.8% purity of felodipine.

Step C. Purification

The crude product was dissolved in MBTE under reflux and the solution cooled linearly over about 3 hours to ambient temperature. The solids were isolated and further washed with MBTE/hexane solution providing 142 g of felodipine (about 37.7% yield, 99.3% purity, MP 144–45° C.).

Example 4

Synthesis of Felodipine Using Benzoic Acid / N-Methylbenzyamine Catalyst System (a) Synthesis of MBI A single necked 1-L flask charged with 2,3-dichlorobenzaldehyde (87.5 g, 0.5 mol), of benzoic acid (3.66 g, 0.030 mol), isopropanol (662 mL), methyl acetoacetate (64.0 g, 0.55 mol), and N-methylbenzylamine (3.6 g, 0.030 mol). The flask was placed on a rotary evaporator equipped with a thermowell (via steam duct) for monitoring internal temperature and the flask heated and agitated to bring flask contents up to 55–65° C. for approximately 4–5 hours. The mixture was concentrated by removing 250–350 g of distillate at about 45–65° C. (internal temperature) and the contents gradually cooled in an ice bath to about 0–5° C. The precipitated MBI solids were isolated by filtration and washed with about isopropanol (75–80 g). The washings were combined with the filtrate. The combined filtrates and washings were re-heated to 55–65° C. for one hour, and concentrated by removing about 175–225 g of the distillate at about 45–65° C. (internal temperature). The contents were again gradually cooled in an ice bath to collect a second crop of MBI solids which were isolated by filtration on the same filter funnel containing the first crop of solids. The combined first and second crop solids were washed with 4×80 g of isopropanol and dried in vacuo at ambient temperature. This gave MBI as a white solid (81.7 g, 59.9% yield based on dichlorobenzaldehyde). LC analysis showed 99.89% MBI [95.73% A-isomer+4.16% B-isomer].

(b) Synthesis of Felodipine from MBI

A 3-L flask was equipped with a mechanical agitator, nitrogen purge, reflux condenser, addition funnel, and internal temperature probe was charged with the MBI solids (81.7 g, 0.30 mol), isopropanol (217 mL) and the contents are brought to reflux. A solution of ethyl 3-aminocrotonate (31.8 g, 0.25 mol, 0.83 equiv) in isopropanol (102 mL) was added to the refluxing solution at such a rate that the internal temperature was maintained at reflux (ca. 83–85° C. during 10 minute addition). The resulting mixture was kept at reflux for 70 minutes, then the temperature was brought down to below 50° C. by: (1) removing heat source, (2) adding isopropanol (102 mL), and (3) vacuum distillation of isopropanol. The vacuum distillation was performed at below 50° C. to remove approximately 200–300 grams of distillate. Cyclohexane (170 g) was added to the residue and the distillation continued at below 50° C. to remove and additional 100–200 g of distillate. Another cyclohexane (170 g) portion was added to the residue and the distillation continued at below 50° C. to remove yet another 100–200 g of distillate. A third cyclohexane (800 g) was added and the contents brought to atmospheric reflux (83–85° C.) for about 16 hours. The slurry was cooled to about 30–35° C. and the crude felodipine isolated by filtration and washed with cyclohexane (76 mL).

(c) Purification

The moist crude felodipine solids were dissolved in methyl t-butylether (MTBE) (810 mL) and hot filtered to clarify the solution. The dissolving flask and filter were rinsed with an additional MTBE (40 mL), which was added to the original hot filtrate. The MTBE solution was placed in a flask equipped with an agitator, nitrogen purge, heat source, temperature probe, distillation head, and receiver. The mixture was concentrated by atmospheric distillation to remove MTBE (internal temperature about 57° C.). Once 200–300 g of distillate was collected, cyclohexane was added in an amount to prepare approximately an 80:20 (w/w) MTBE:cyclohexane solvent system. The resultant solution was cooled and the recrystallized. Felodipine was isolated at about 30–35° C. The recrystallized felodipine solids were further washed with a MTBE/cyclohexane mixture (10 g MTBE+40 g cyclohexane) and cyclohexane (90 mL). The solids were dried in vacuo to afford pure Felodipine as a light yellow crystalline solid (56.9 g, 59.4% yield based on ethyl 3-aminocrotonate).

Example 5

Synthesis of MBI Using Phenylacetic Acid/N-Methylbenzylamine Catalyst System

A single necked 1-L flask charged with 2,3-dichlorobenzaldehyde (87.5 g, 0.5 mol), phenylacetic acid (4.08 g, 0.030 mol), isopropanol (662 mL), methyl acetoacetate (64.0 g, 0.55 mol), and N-methylbenzylamine (3.6 g, 0.030 mol). The flask was placed on a rotary evaporator equipped with a thermowell (via steam duct) for monitoring internal temperature and the flask heated and agitated to bring flask contents up to 55–65° C. for approximately 4–5 hours. The mixture was concentrated by removing 250–350 g of distillate at about 45–65° C. (internal temperature) and the contents gradually cooled in an ice bath to about 0–5° C. The precipitated MBI solids were isolated by filtration and washed with about isopropanol (75–80 g). The washings were combined with the filtrate. The combined filtrates and washings were re-heated to 55–65° C. for one hour, and concentrated by removing about 175–225 g of the distillate at about 45–65° C. (internal temperature). The contents were again gradually cooled in an ice bath to collect a second crop of MBI solids which were isolated by filtration on the same filter funnel containing the first crop of solids. The combined first and second crop solids were washed with 4×80 g of isopropanol and dried in vacuo at ambient temperature. This gave MBI as a white solid (85.2 g, 62.4% Yield based on dichlorobenzaldehyde). LC analysis showed 99.91% MBI [97.63% A-isomer+2.28% B-isomer].

Example 6

Synthesis of MBI Using Chloroacetic Acid/Diethylamine Catalyst System

A single necked 1-L flask charged with 2,3-dichlorobenzaldehyde (87.5 g, 0.5 mol), chloroacetic acid (2.84 g, 0.030 mol), isopropanol (662 mL), methyl acetoacetate (64.0 g, 0.55 mol), and diethylamine (2.2 g, 0.030 mol). The flask was placed on a rotary evaporator equipped with a thermowell (via steam duct) for monitoring internal temperature and the flask heated and agitated to bring flask contents up to 55–65° C. for approximately 16 hours. The mixture was concentrated by removing 250–350 g of distillate at about 45–65° C. (internal temperature) and the contents gradually cooled in an ice bath to about 0–5° C. The precipitated MBI solids were isolated by filtration and washed with about isopropanol (75–80 g). The filtrate was discarded and the MBI crystals were washed further with isopropanol (2×80 g) and dried in vacuo at ambient temperature. This gave MBI as an off-white solid (84.7 g, 62.0% Yield based on dichlorobenzaldehyde). LC-Analysis showed 99.76% MBI [97.3% A-isomer+2.46% B-isomer].

We claim:

1. A process for the preparation of a dihydropyridine compound comprising:

(a) contacting an aldehyde compound having the formula

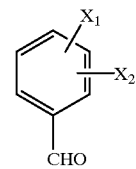

wherein $X_1$ and $X_2$ are the same or different substituents selected from the group consisting of H, $C_{1-6}$ alkyl, $C_{1-6}$ alkoxy, $C_{1-6}$ alkylaryl, halo, aryl, and substituted aryl, with a compound having the formula wherein Y is COOR, wherein R is $C_{1-6}$ alkyl, and a catalytic amount of a mixture of (I) a carboxylic acid compound having the formula $R_1$—$C(R_2, R_3)$—COOH or

[structure: benzene ring with Z and COOH substituents, and $R_{1-3}$]

wherein $R_1$, $R_2$, and $R_3$ are independently selected from H, halogen, $C_{1-6}$ alkyl, $C_{1-6}$ alkoxy, alkylaryl, aryl and substituted aryl wherein substituents may be in any position; Z is independently selected from H, halogen, $NO_2$, $OCH_3$, and OH, and (II) a substituted or unsubstituted secondary amine, to form a benzylidene intermediate;

(b) contacting said benzylidene intermediate with a suitably substituted enamine in the absence of an acid to form the dihydropyridine compound and isomers thereof: and (c) purifying said dihydropyridine compound by contacting the dihydropyridine compound and isomers thereof with a refluxing inert solvent, said solvent having a boiling point of at least about 80° C. for a sufficient period of time to convert the isomers to the dihydropyridine compound.

2. A process for the preparation of felodipine comprising:
(a) contacting 2,3-dichlorobenzaldehyde, methyl acetoacetate, and a catalytic amount of a mixture of (I) a carboxylic acid compound having the formula $R_1$—C$(R_2,R_3)$—COOH or

[structure: benzene ring with Z and COOH substituents, and $R_{1-3}$]

wherein $R_1$, $R_2$, and $R_3$ are independently selected from H, halogen, $C_{1-6}$ alkyl, $C_{1-6}$ alkoxy, alkylaryl, aryl and substituted aryl wherein substituents may be in any position; Z is independently selected from H, halogen, $NO_2$, $OCH_3$, and OH, and (II) a substituted or unsubstituted secondary amine, to form a benzylidene intermediate;

(b) contacting said benzylidene intermediate with ethyl aminocrotonate in the absence of an acid to form felodipine and isomers thereof; and (c) purifying said felodipine by contacting the felodipine and isomers thereof with a refluxing inert solvent, said solvent having a boiling point of at least about 80° C., for a sufficient period of time to convert the isomers to felodipine.

3. The process of claim 2 wherein step (b) occurs in an alcoholic solvent.

4. The process of claim 3 wherein the solvent is selected from the group consisting of $C_{1-6}$ alcohol.

5. The process of claim 2 wherein suitable reaction conditions for step (a) comprise a temperature range of about 45° C. to about 65° C.

6. The process of claim 2 wherein suitable reaction conditions for step (a) comprise a reaction time of about 3 to about 18 hours.

7. The process of claim 2 wherein suitable reaction conditions for step (b) comprise a temperature range of about reflux of the solvent employed.

8. The process of claim 7 wherein suitable reaction conditions further comprise a reaction time of less than about 1 hour.

9. The process of claim 1 wherein the aldehyde is selected from the group consisting of 2-nitrobenzaldehyde, 3-nitrobenzaldehyde, 2, 1, 3-benzoxadiazole-4-aldehyde.

10. The process of claim 1 wherein the secondary amine is selected from the group consisting of N-methylbenzylamine, diethylamine, dimethylamine, isopropylethylamine, isopropylmethylamine.

11. The process of claim 2 wherein the catalyst mixture is as carboxylate salt of an amine.

12. The process of claim 2 wherein the catalyst mixture is a benzoate salt of an amine.

13. The process of claim 2 wherein the aldehyde is selected from the group consisting of 2-nitrobenzaldehyde, 3-nitrobenzaldehyde, 2, 1, 3-benzoxadiazole-4-aldehyde.

14. The process of claim 2 wherein the secondary amine is selected from the group consisting of N-methylbenzylamine, diethylamine, dimethylamine, isopropylethylamine, isopropylmethylamine.

15. The process of claim 1, wherein said carboxylic acid compound is selected from the group consisting of chloroacetic acid, phenylacetic acid, dichloroacetic acid and benzoic acid.

16. The process of claim 2, wherein said carboxylic acid compound is selected from the group consisting of chloroacetic acid, phenylacetic acid, dichloroacetic acid and benzoic acid.

17. A process for the preparation of a dihydropyridine compound comprising:
(a) contacting an aldehyde compound having the formula

[structure: benzene ring with $X_1$, $X_2$, and CHO substituents]

wherein $X_1$ and $X_2$ are the same or different substituents selected from the group consisting of H, $C_{1-6}$ alkyl, $C_{1-6}$ alkoxy, $C_{1-6}$ alkylaryl, halo, aryl, and substituted aryl, with a compound having the formula

[structure: Y—CH(—)—C(=O)—]

wherein Y is COOR, wherein R is $C_{1-6}$ alkyl, and a catalytic amount of a mixture of (I) a carboxylic acid compound selected from the group consisting of chloroacetic acid, dichloro acetic acid and benzoic acid, and (II) a substituted or unsubstituted secondary amine, to form a benzylidene intermediate;

(b) contacting said benzylidene intermediate with a suitably substituted enamine in the absence of an acid to form the dihydropyridine compound and isomers thereof; and (c) purifying said dihydropyridine compound by contacting the dihydropyridine compound and isomers thereof with a refluxing inert solvent, said solvent having a boiling point of at least about 80° C., for a sufficient period of time to convert the isomers to the dihydropyridine compound.

18. The process of claim 17, wherein step (b) occurs in an alcoholic solvent.

19. The process of claim 17, wherein suitable reaction conditions for step (b) comprise a temperature range of about reflux of the solvent employed.

* * * * *